(12) United States Patent
Ellingson et al.

(10) Patent No.: US 8,433,408 B2
(45) Date of Patent: Apr. 30, 2013

(54) PACING IN THE PRESENCE OF ELECTROMAGNETIC INTERFERENCE

(75) Inventors: Michael L. Ellingson, St. Louis Park, MN (US); Hyun J. Yoon, Vadnais Heights, MN (US); Patrick L. Parish, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 41 days.

(21) Appl. No.: 13/095,076

(22) Filed: Apr. 27, 2011

(65) Prior Publication Data

US 2012/0277817 A1 Nov. 1, 2012

(51) Int. Cl.
*A61N 1/00* (2006.01)
(52) U.S. Cl.
USPC .......................................................... 607/27
(58) Field of Classification Search ................. 607/4–28
See application file for complete search history.

(56) References Cited

U.S. PATENT DOCUMENTS

| | | |
|---|---|---|
| 5,522,857 A | 6/1996 | van Krieken |
| 5,647,379 A | 7/1997 | Meltzer |
| 5,697,958 A | 12/1997 | Paul et al. |
| 6,188,926 B1 | 2/2001 | Vock |
| 7,082,328 B2 | 7/2006 | Funke |
| 7,693,568 B2 | 4/2010 | Zeijlemaker |
| 2003/0144705 A1 | 7/2003 | Funke |
| 2005/0070787 A1 | 3/2005 | Zeijlemaker |
| 2007/0238975 A1 | 10/2007 | Zeijlemaker |
| 2010/0106209 A1 | 4/2010 | Gunderson et al. |
| 2010/0152805 A1 | 6/2010 | Zeijlemaker |

FOREIGN PATENT DOCUMENTS

WO 2005035048 A2 4/2005

OTHER PUBLICATIONS (PCT/US2012/020406) PCT Notification of Transmittal of the International Search Report and the Written Opinion of the International Searching Authority, 11 pages.

*Primary Examiner* — Scott Getzow
(74) *Attorney, Agent, or Firm* — Stephen W. Bauer; Michael J. Ostrom

(57) ABSTRACT

This disclosure provides a pacing technique that reduces the effect of oversensing caused by noise on pacing therapy. The IMD delivers a pacing pulse subsequent to sensing an electrical signal on the lead when the sensed electrical signal coincides with an independently detected noise signal and the sensed electrical signal occurs during a period of time of an expected intrinsic cardiac signal. The IMD may, in some instances, trigger delivery of the pacing pulse during the escape interval instead of waiting for the escape interval to expire. Pacing in accordance with the techniques of this disclosure may allow for improved therapy during an MRI procedure by decreasing the risk associated with inappropriate pacing inhibition as well as decreasing the risk associated with pacing during the vulnerable period of the cardiac cycle.

19 Claims, 6 Drawing Sheets

PACING IN THE PRESENCE OF ELECTROMAGNETIC INTERFERENCE

TECHNICAL FIELD

This disclosure relates generally to implantable medical systems. More particularly, this disclosure describes techniques for pacing in the presence of electromagnetic interference (EMI).

BACKGROUND

A wide variety of implantable medical systems that deliver a therapy or monitor a physiologic condition of a patient have been clinically implanted or proposed for clinical implantation in patients. The implantable medical system may include an implantable medical lead connected to an implantable medical device (IMD). For example, implantable leads are commonly connected to implantable pacemakers, defibrillators, cardioverters, or the like, to form an implantable cardiac system that provides electrical stimulation to the heart or sensing of electrical activity of the heart. The electrical stimulation pulses can be delivered to the heart and the sensed electrical signals can be sensed by electrodes disposed on the leads, e.g., typically near distal ends of the leads. Implantable leads are also used in neurological devices, muscular stimulation therapy, gastric system stimulators and other implantable medical devices (IMDs).

Patients that have implantable medical systems may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static magnetic field may be generated by a primary magnet within the MRI device and may be present prior to initiation of the MRI procedure. The gradient magnetic fields may be generated by electromagnets of the MRI device and may be present during the MRI procedure. The RF fields may be generated by transmitting/receiving coils of the MRI device and may be present during the MRI procedure. If the patient undergoing the MRI procedure has an implantable medical system, the various fields produced by the MRI device may have an effect on the operation of the medical leads and/or the IMD to which the leads are coupled. For example, the gradient magnetic fields or the RF fields generated during the MRI procedure may induce energy on the implantable leads (e.g., in the form of an electrical current), which may cause oversensing by the IMD. In other words, the IMD may incorrectly detect a cardiac signal when one is not present. Oversensing may result in the IMD delivering therapy when it is not desired or withholding therapy when it is desired.

A number of techniques have been described for reducing the effects of oversensing during an MRI procedure. For example, U.S. Pat. No. 7,693,568 to Zeijlemaker (referred to herein as "the '568 patent") describes a signal processing algorithm for discounting MRI artifacts. As described with reference to FIG. 5B of the '568 patent, when electrical activity and gradient field activity are sensed, per step 402, a decision is made at step 403 based upon the timing of the sensed electrical events. If electrical events, for example sensed by electrodes of a lead, do not coincide with gradient field activity whether or not the electrical events coincide with extrapolated cardiac events, the events are counted as an actual cardiac event at step 404C. If sensed electrical events do coincide with the sensed gradient fields but not with extrapolated cardiac events, the events are counted as noise at step 404B. If sensed electrical events coincide with both of the extrapolated cardiac events and the sensed gradient fields, the events are counted as "virtual" or potential cardiac events at step 404A. The "virtual" events are processed by the device, according to typical state of the art limitations for such devices, for control of therapy delivery to maintain physiological cardiac function. Per step 405, when a consecutive count of noise events and "virtual" cardiac events exceeds a predetermined number, electrical sensing is ignored at step 406. If electrical sensing is ignored, then the device may switch into a prescribed mode of therapy delivery, for example pacing stimulation at a prescribed number of beats per minute.

As another example, U.S. Pat. No. 5,697,958 to Paul et al. (referred to herein as "the '958 patent") describes a demand pacemaker that responds to a message that electromagnetic interference (EMI) has been detected in the same manner that it would respond if it sensed that the heart of the patient has failed to perform an expected event, that is, by producing a pacing signal to pump the chamber in which heart signals are being sensed. With reference to FIG. 7 of the '958 patent, upon the start 210 of the illustrated process 200 the microprocessor initiates an escape interval at 212, that is, a time interval during which the pacemaker waits for the heart to perform an event, such as producing a cardiac electrical signal, for the pacemaker to sense and during which the pacemaker will not send a pacing signal to the heart. At 214 the pacemaker waits for the escape interval to expire, or the pacemaker to sense an event at the heart, whichever occurs first. The microprocessor inquires at 216 whether a heart event was sensed by the expiration of the escape interval.

If the answer is affirmative, the microprocessor of the '958 patent proceeds from 216 to determine at 218 whether it has received an "EMI present" flag, or an EMI coincidence flag, for example, from the noise detector of the present invention during the time period since the start of the escape interval at 212. If EMI is not present, a conclusion is reached that the pacemaker is functioning properly and the sensed signal is a true indication of the occurrence of the heart event and steps 220-224 are performed. However, if EMI is determined at 218 to be present, the microprocessor cannot know whether the signal sensed by the pacemaker was actually the result of a heart event or the result of EMI in the pacemaker electronics. Therefore, if EMI is determined at 218 to be present, the pacemaker proceeds as if the patient needed assistance. The pacemaker waits at 228 for the current escape time interval to be completed and generates a stimulus pulse at 226.

SUMMARY

This disclosure provides a pacing technique that reduces the effect of oversensing caused by noise on pacing therapy. As will be described in further detail below, the IMD controls pacing therapy based on whether an electrical signal sensed on one of the leads coincides with an independently detected noise signal and occurs during a period of time of an expected intrinsic cardiac signal. The IMD delivers a pacing pulse subsequent to sensing an electrical signal on the lead when the sensed electrical signal coincides with an independently detected noise signal and the sensed electrical signal occurs during a period of time of an expected intrinsic cardiac signal. The IMD may, in some instances, trigger delivery of the pacing pulse during the escape interval instead of waiting for the escape interval to expire. Pacing in accordance with the techniques of this disclosure may allow for improved therapy during an MRI procedure by decreasing the risk associated with inappropriate pacing inhibition as well as decreasing the risk associated with pacing during the vulnerable period of the cardiac cycle.

In one example, this disclosure is directed to a method comprising sensing an electrical signal on an implantable medical lead, determining whether the sensed electrical signal coincides with a sensed noise signal, determining whether the sensed electrical signal occurs during a period of time of an expected intrinsic cardiac signal, and triggering delivery of a pacing pulse before expiration of an escape interval when the sensed electrical signal coincides with a sensed noise signal and the sensed electrical signal occurs during the period of time of the expected intrinsic cardiac signal.

In another example, this disclosure is directed to an implantable medical system comprising an implantable medical lead including at least one electrode and an implantable medical device coupled to the implantable medical lead. The implantable medical device comprise a noise detection module that detects noise signals, a sensing module that detects an electrical signal on the implantable medical lead, a therapy module that delivers pacing therapy via the implantable medical lead, and a control module. The control module determines whether the sensed electrical signal coincides with a sensed noise signal, determines whether the sensed electrical signal occurs during a period of time of an expected intrinsic cardiac signal, and controls the therapy module to deliver a pacing pulse before expiration of an escape interval when the sensed electrical signal coincides with a sensed noise signal and the sensed electrical signal occurs during the period of time of the expected intrinsic cardiac signal.

In a further example, this disclosure is directed to a computer-readable medium comprising instructions that, when executed, cause an implantable medical device to sense an electrical signal on an implantable medical lead, determine whether the sensed electrical signal coincides with a sensed noise signal, determine whether the sensed electrical signal occurs during a period of time of an expected intrinsic cardiac signal, and trigger delivery of a pacing pulse before expiration of an escape interval when the sensed electrical signal coincides with a sensed noise signal and the sensed electrical signal occurs during the period of time of the expected intrinsic cardiac signal.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
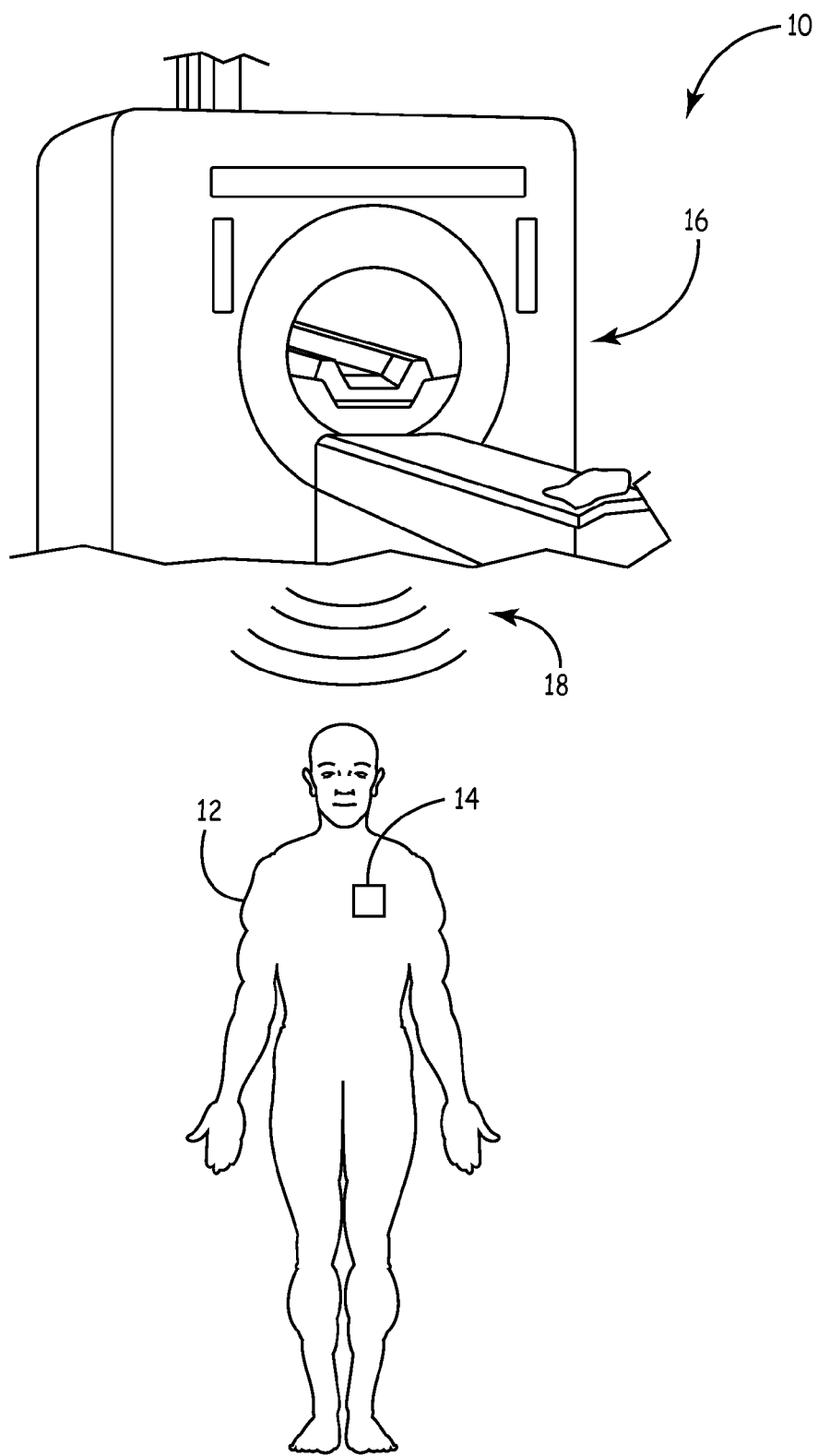
FIG. 1 is a conceptual diagram illustrating an environment in which a patient with an implantable medical system is exposed to external fields.

FIG. 1 is a conceptual diagram illustrating an environment 10 in which a patient 12 with an implantable medical system 14 is exposed to an external field 18. In the example illustrated in FIG. 1, environment 10 includes an MRI device 16 that generates external field 18. MRI device 16 generates magnetic and RF fields to produce images of body structures for diagnosing injuries, diseases and/or disorders. In particular, MRI device 16 generates a static magnetic field, gradient magnetic fields and RF fields as is well known in the art. The static magnetic field is a large non time-varying magnetic field that is typically always present around MRI device 16 whether or not an MRI procedure is in progress. Gradient magnetic fields are pulsed magnetic fields that are typically only present while the MRI procedure is in progress. RF fields are pulsed high frequency fields that are also typically only present while the MRI procedure is in progress.

The magnitude, frequency or other characteristic of the static magnetic field, gradient magnetic fields and RF fields may vary based on the type of MRI device producing the field or the type of MRI procedure being performed. A 1.5 T MRI device, for example, will produce a static magnetic field of about 1.5 Tesla (T) and have a corresponding RF frequency of about 64 megahertz (MHz) while a 3.0 T MRI device will produce a static magnetic field of about 3.0 Tesla and have a corresponding RF frequency of about 128 MHz. However, other MRI devices may generate different fields.

Implantable medical system 14 may, in one example, include an IMD connected to one or more leads. The IMD may be an implantable cardiac device that senses electrical activity of a heart of patient 12 and/or provides electrical stimulation therapy to the heart of patient 12. For example, the IMD may be an implantable pacemaker, implantable cardioverter defibrillator (ICD), cardiac resynchronization therapy defibrillator (CRT-D), cardioverter device, or combinations thereof. The IMD may alternatively be a non-cardiac implantable device, such as an implantable neurostimulator or other device that provides electrical stimulation therapy.

During an MRI procedure patient 12 may be placed at least partially within a bore of MRI device 16. Some or all of the various types of fields produced by MRI device 16 (which are represented by external field 18) may create electromagnetic interference (EMI) that has undesirable effects on implantable medical system 14. In one example, the gradient magnetic fields and/or the RF fields generated during the MRI procedure may induce energy on the conductors of the leads (e.g., in the form of a current). The induced energy on the leads may be conducted to the IMD and inappropriately detected as physiological signals, a phenomenon often referred to as oversensing. The detection of the induced energy on the leads as physiological signals may result in the IMD delivering therapy when it is not desired (e.g., triggering a pacing pulse) or withholding therapy when it is desired (e.g., inhibiting a pacing pulse).

This disclosure provides a pacing technique that reduces the effect of oversensing caused by EMI on pacing therapy. As will be described in further detail below, the IMD controls pacing therapy based on whether an electrical signal sensed on one of the leads coincides with an independently detected noise signal and occurred during a period of time of an expected intrinsic cardiac signal. Such a technique more accurately distinguishes actual cardiac signals from induced signals caused by EMI. Pacing in accordance with the techniques of this disclosure may allow for improved therapy during an MRI procedure by decreasing the risk associated with inappropriate pacing inhibition as well as decreasing the risk associated with pacing during the vulnerable period of the cardiac cycle.

In some instances, the IMD may operate in accordance with the described pacing mode as a normal mode of operation. In this case, pacing in accordance with the techniques of this disclosure could also eliminate the service burden associated with manually programming an MRI safe mode of operation before and after a patient undergoes a MRI procedure. In other instances, the IMD may be configured to operate in the described pacing mode upon detecting the presence of MRI device 16 or manually before undergoing the MRI procedure.

Figure 2:
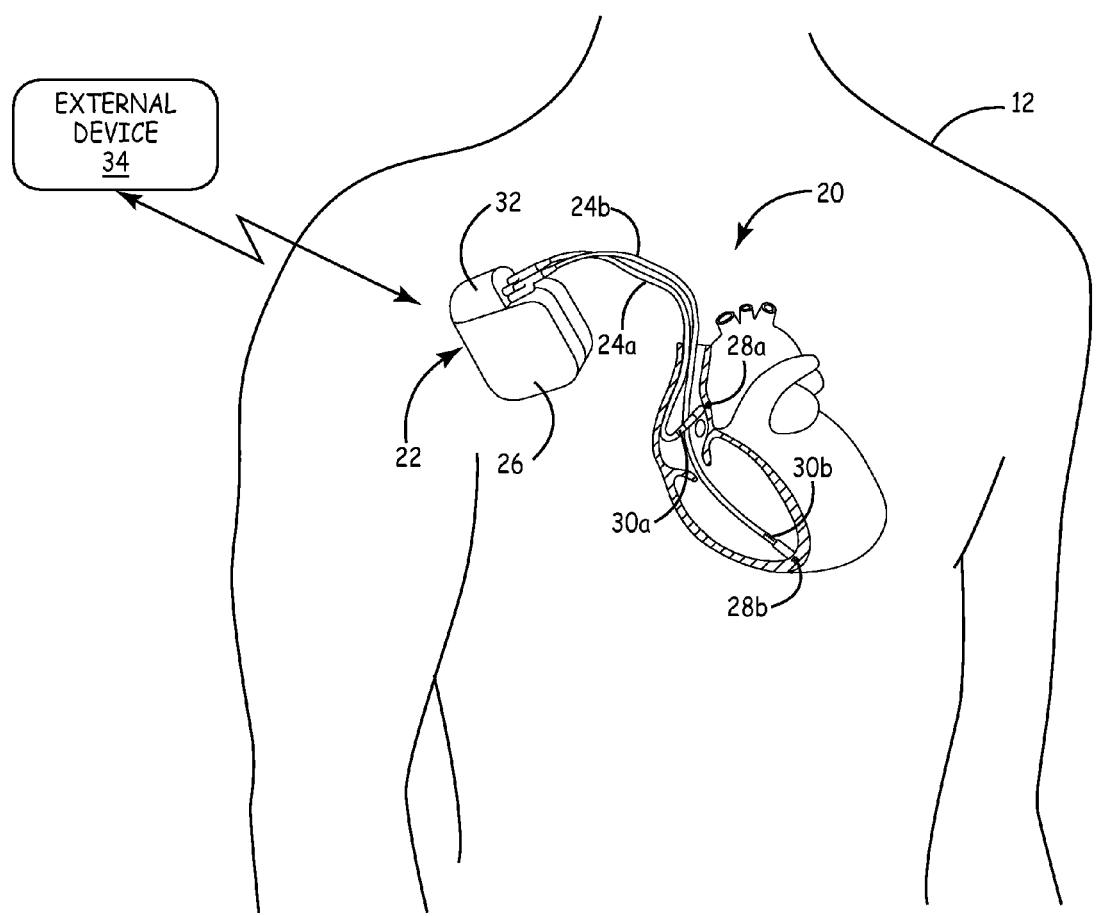
FIG. 2 is a conceptual diagram illustrating an example implantable medical system.

FIG. 2 is a conceptual diagram illustrating an example implantable medical system 20. Implantable medical system 20 may correspond with implantable medical system 14 of FIG. 1. Implantable medical system 20 includes an IMD 22 connected to leads 24a,b. IMD 22 includes a housing 26 within which electrical components and a power source of IMD 22 are housed. Housing 26 can be formed from conductive materials, non-conductive materials or a combination thereof. As will be described in further detail herein, housing 26 may house one or more processors, memories, transmitters, receivers, transceivers, sensors, sensing circuitry, therapy circuitry, antennas and other components.

Leads 24a,b each includes one or more electrodes. In the example illustrated in FIG. 2, leads 24a,b each include a respective tip electrode 28a,b and ring electrode 30a,b located near a distal end of their respective leads 24a,b. When implanted, tip electrodes 28a,b and/or ring electrodes 30a,b are placed relative to or in a selected tissue, muscle, nerve or other location within the patient 12. In the example illustrated in FIG. 2, tip electrodes 28a,b are extendable helically shaped electrodes to facilitate fixation of the distal end of leads 24a,b to the target location within patient 12. In this manner, tip electrodes 28a,b are formed to define a fixation mechanism. In other embodiments, one or both of tip electrodes 28a,b may be formed to define fixation mechanisms of other structures. In other instances, leads 24a,b may include a fixation mechanism separate from tip electrode 28a,b. Fixation mechanisms can be any appropriate type, including a grapple mechanism, a helical or screw mechanism, a drug-coated connection mechanism in which the drug(s) serves to reduce infection and/or swelling of the tissue, or other attachment mechanism.

Leads 24a,b are connected at a proximal end to IMD 22 via connector block 32. Connector block 32 may include one or more receptacles that interconnect with one or more connector terminals located on the proximal end of leads 24a,b. Leads 24a,b are ultimately electrically connected to one or more of the electrical components within housing 26.

One or more conductors (not shown in FIG. 2) extend within leads 24a,b from connector block 32 along the length of the lead to engage the ring electrode 30a,b and tip electrode 28a,b, respectively. In this manner, each of tip electrodes 28a,b and ring electrodes 30a,b is electrically coupled to a respective conductor within its associated lead bodies. For example, a first electrical conductor can extend along the length of the body of lead 24a from connector block 32 and electrically couple to tip electrode 28a and a second electrical conductor can extend along the length of the body of lead 24a from connector block 32 and electrically couple to ring electrode 30a. The respective conductors may electrically couple to circuitry, such as a therapy module or a sensing module, of IMD 22 via connections in connector block 32. IMD 22 delivers therapy to the heart (or other location) via the electrical conductors to one or more of electrodes 28a,b and 30a,b and receives sensed electrical signals on the electrical conductors from one or more of electrodes 28a,b and 30a,b.

IMD 22 may communicate with external device 34 to exchange data with external device 34. External device 34 may, for example, communicate with IMD 22 to provide one more operating parameters for operation of IMD 22. IMD 22 may also transmit sensed physiological data, diagnostic determinations made based on the sensed physiological data, IMD performance data and/or IMD integrity data to external device 34. IMD 22 and external device 34 may communicate via wireless communication using any techniques known in the art. Examples of communication techniques may include, for example, inductive telemetry or RF telemetry, although other techniques are also contemplated.

The configuration of implantable medical system 20 illustrated in FIG. 2 is merely an example. In other examples, implantable medical system 20 may include more or fewer leads extending from IMD 22. For example, IMD 22 may be coupled to three leads, e.g., a third lead implanted within a left ventricle of the heart of the patient. In another example, IMD 22 may be coupled to a single lead that is implanted within either an atrium or ventricle of the heart of the patient. As such, IMD 22 may be used for single chamber or multi-chamber cardiac rhythm management therapy.

In addition to more or fewer leads, each of the leads may include more or fewer electrodes. In instances in which IMD 22 is used for therapy other than pacing, e.g., defibrillation or cardioversion, the leads may include elongated electrodes, which may, in some instances, take the form of a coil. IMD 22 may deliver defibrillation or cardioversion shocks to the heart via any combination of the elongated electrodes and housing electrode. As another example, medical system 20 may include leads with a plurality of ring electrodes, e.g., as used in some implantable neurostimulators, without a tip electrode or with one of the ring electrodes functioning as the "tip electrode."

Figure 3:
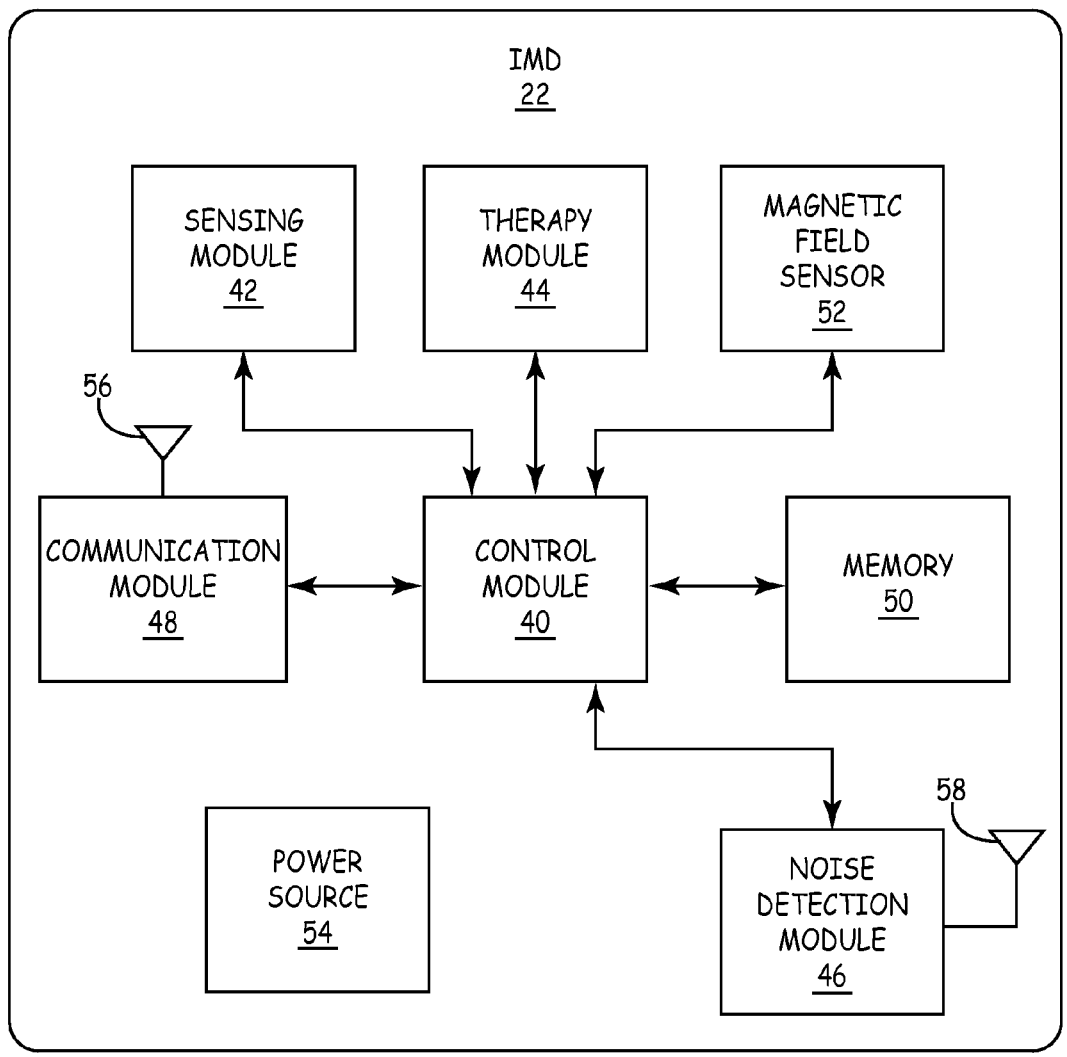
FIG. 3 is a functional block diagram of an example configuration of electronic components of an implantable medical device.

FIG. 3 is a functional block diagram of an example configuration of electronic components of IMD 22. IMD 22 includes a control module 40, sensing module 42, therapy module 44, noise detection module 46, communication module 48, memory 50 and magnetic field sensor 52. The electronic components may receive power from a power source 54, which may be a rechargeable or non-rechargeable battery. In other embodiments, IMD 22 may include more or fewer electronic components. Additionally, any of the described modules or components may be implemented together on a common hardware component or separately as discrete but interoperable hardware or software components. Depiction of different features as modules or components is intended to highlight different functional aspects and does not necessarily imply that such modules or units must be realized by separate hardware or software components. Rather, functionality associated with one or more modules may be performed by separate hardware or software components, or integrated within common or separate hardware or software components.

Memory 50 may include computer-readable instructions that, when executed, cause IMD 22 and/or control module 40 to perform various functions attributed to IMD 22 and control module 40 in this disclosure. In other words, memory 50 includes computer-readable instructions that control operation of IMD 22. Memory 50 may, for example, store operating parameters for any of a number of operating modes, including at least the pacing mode described herein. Memory 50 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, or combination thereof.

Control module 40 may include any one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, control module 40 may include multiple components, such as any combination of one or more microprocessors, one or more controllers, one or more DSPs, one or more ASICs, or one or more FPGAs, as well as other discrete or integrated logic circuitry. The functions attributed to control module 40 herein may be embodied as software, firmware, hardware or any combination thereof.

Control module 40 may control communication module 48 to receive downlink telemetry from and send uplink telemetry to external device 34 with the aid of an antenna 56 of IMD 22. Antenna 56 may be located within connector block 32 of IMD 22 or within housing 26 of IMD 22. In one example, antenna 56 may be an inductive coil antenna within housing 26 of IMD 22. In another example, antenna 56 may be an RF antenna located within connector block 32 and coupled to communication module 48 via a feedthrough. In a further example, IMD 22 may include both an inductive coil antenna and an RF antenna coupled to communication module 48. Communication module 48 includes any suitable hardware, firmware, software or any combination thereof for communicating with another device, such as external device 34 and/or a patient monitor, e.g., by wireless telemetry. For example, communication module 48 may include appropriate modulation, demodulation, frequency conversion, filtering, and amplifier components for transmission and reception of data.

Control module 40 may also control sensing module 42 and therapy module 44 to operate IMD in a programmed operating mode. Sensing module 42 and therapy module 44 are electrically coupled to some or all of electrodes 28a,b and 30a,b via the conductors of leads 24a,b, or to a housing electrode (e.g., formed from or on housing 26) via conductors internal to housing 26. Sensing module 42 is configured to obtain signals sensed via one or more of electrodes 28a,b and 30a,b. Control module 40 may select the electrodes that function as sense electrodes, sometimes referred to as a sensing configuration or sensing vector, in order to monitor electrical activity of the heart. In one example, sensing module 42 may include a switch module (not shown) that control module 40 may configure to select which of the available electrodes to use for sensing the heart activity.

Control module 40 may process the signals from leads 24a,b to monitor electrical activity of the heart of patient 12. Control module 40 may also generate marker channel data based on the detected cardiac activity. For example, marker channel data may include data that indicates the occurrence and timing of sensing, diagnosis, and therapy events associated with patient 12 and/or IMD 22. Control module 40 may store signals obtained by sensing module 42 as well as any generated EGM waveforms, marker channel data or other data derived based on the sensed signals in memory 50. Control module 40 may analyze the EGM waveforms and/or marker channel data to detect cardiac events (e.g., tachyarrhythmias). Control module 40 may also later retrieve stored EGMs and/or marker channel data from memory 50, e.g., upon a request from external device 34 received via communication module 48. In further examples, sensing module 42 is coupled to one or more sensors that are not included on leads 24a,b, e.g., via a wired or wireless coupling. Such sensors may include pressure sensors, accelerometers, flow sensors, blood chemistry sensors, activity sensors, magnetic field sensors or other types of physiological sensors.

Therapy module 44 is configured to generate and deliver electrical stimulation therapy to the heart. Control module 40 may control therapy module 44 to deliver electrical stimulation therapy to the heart via one or more of electrodes 28a,b and 30a,b according to one or more therapy programs, which may be stored in memory 50. Control module 40 controls therapy module 44 to deliver electrical pacing pulses, cardiac resynchronization pacing pulses, cardioversion pulses, or defibrillation pulses with the amplitudes, pulse widths, frequencies, electrode combinations or electrode configuration specified by a selected therapy program. In the case of pacing, for example, therapy module 44 may deliver pacing pulses via a bipolar electrode configuration, e.g., using electrodes 28a,b and ring electrodes 30a,b. In other instances, therapy module 44 may deliver pacing pulses via a unipolar electrode configuration, e.g., using electrodes 28a,b and a housing electrode of IMD 22. Therapy module 44 may include a switch module (not shown and which may be the same or different switch module described above with respect to sensing module 42). Control module 40 may configure the switch module to select which of the available electrodes are used to deliver the stimulation therapy. Therapy module 44 may deliver one or more of these types of stimulation in the form of other signals besides pulses or shocks, such as sine waves, square waves, or other substantially continuous signals.

Control module 40 or therapy module 44 may include pacer timing and control circuitry, which may be embodied as hardware, firmware, software, or any combination thereof. The pacer timing and control circuitry may comprise a dedicated hardware circuit, such as an ASIC, DSP or processor, separate from other components of control module 40 or therapy module 44, or a software module executed by a component of control module 40 or therapy module 44.

The pacer timing and control circuitry may include programmable counters which control the basic time intervals associated with various single and dual chamber pacing modes. Intervals defined by the pacer timing and control circuitry may include, for example, atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals to sensing module 42 to blank one or more channels, e.g., amplifiers, for a period during and after delivery of electrical stimulation to the heart. The durations of these intervals may be determined by control module 40 in response to stored program data in memory 50. The pacer timing and control circuitry may also determine the amplitude of the cardiac pacing pulses.

The escape intervals define time intervals during which IMD 22 waits to sense a cardiac event, such as an intrinsic cardiac depolarization of a respective chamber of the heart, before delivering a pacing pulse to the heart. In particular, IMD 22 waits to sense a cardiac event in the atrium during the atrial escape interval and waits to sense a cardiac event in the ventricle during the ventricular escape interval. Control module 40 controls therapy module 44 to deliver a pacing pulse to the heart when the escape interval expires and no cardiac event has been sensed. Control module 40 may reset the escape interval counters within the pacer timing and control circuitry upon sensing of cardiac events with detection channels of sensing module 42.

A patient having implanted medical system 20 may receive a certain therapy or diagnostic technique that exposes implantable medical system 20 to external fields, such as external fields 18 of FIG. 1. In the case of an MRI procedure, for example, implantable medical system 20 is exposed to high frequency RF pulses and various magnetic fields to create image data regarding the patient 12. The RF pulses and/or gradient magnetic fields can induce currents on the conductors of leads 24a,b of the IMD 22. The current induced on leads 24a,b can be conducted to electrical components of IMD 22 and detected as cardiac signals, thereby causing oversensing. In conventional pacemakers, the current induced on the leads may cause the IMD to reset the atrial and/or ventricular escape interval counters when no intrinsic cardiac event actually occurs, thereby inhibiting delivery of desired pacing pulses.

In accordance with the pacing techniques described in this disclosure, control module 40 utilizes a recent history of cardiac electrophysiological data and mechanisms to independently detect noise in order to provide more appropriate pacing therapy in the presence of EMI. Control module 40 determines periods of time around which intrinsic cardiac signals are expected to occur. Control module 40 may, for example, determine the periods of time for the expected intrinsic cardiac signals based on the recent history of heart rate, heart rate variability, pacing percentage, and the like. In this manner, control module 40 determines windows of time during which intrinsic cardiac events are expected to occur. The determined periods of time around which intrinsic cardiac signals are expected to occur may, in some instances, be less than the escape interval. In some instances, the end of the escape interval and the end of the period of time around which intrinsic cardiac signals are expected to occur are substantially the same. The periods of time around which intrinsic cardiac signals are expected to occur may be on the order of a few hundred milliseconds in duration in one example.

Noise detection module 46 of IMD 22 independently detects noise signals separately from the signals detected on leads 24a,b. Noise detection module 46 may, for example, receive noise signals by means of at least one antenna 58. In some instances, IMD 22 may include an antenna capable of detecting both RF fields and gradient magnetic fields. In other instances, IMD 22 may include one antenna for detecting the RF fields generated by MRI device 16 and another antenna for detecting gradient magnetic fields generated by MRI device 16.

Antenna 58 of noise detection module 46 may be the same as antenna 56 of communication module 48, e.g., an inductive coil antenna, RF antenna or the like. For example, the signal received on antenna 56/58 may be divided and provided to communication module 48 and noise detection module 46. In another example, noise detection module 46 and communication module 48 may be a single module that analyzes the signals received on the antenna. Thus, noise signals that are induced in the telemetry antenna are detected and appropriately processed as described in further detail herein. In instances in which IMD 22 includes both an inductive coil antenna and an RF antenna, noise detection module 46 may be coupled to both.

In another example, antenna 58 may be at least one separate, dedicated antenna. One example antenna is described in U.S. Pat. No. 7,693,568 to Zeijlemaker, which is incorporated herein for its description of transducer 40 that detects MRI gradient magnetic fields. Transducer 40 of the '568 patent can detect an MRI gradient magnetic field via inductive coupling of the field with one of three orthogonal coils 41, 42, 43, depending upon the orientation of the field. Coils 41, 42, 43 of transducer 40 of the '568 patent are sensitive enough to detect small changes in the magnetic field, for example, between approximately 5 Tesla per second and approximately 300 Tesla per second.

In a further example, antenna 58 may be a different one of leads 24 than the lead on which the electrical signals are being monitored. For example, an atrial lead may be utilized as noise antenna for determining whether sensed electrical signal on ventricular lead coincides with noise. In this case, noise detection module 46 may be a part of the sensing module 42.

Control module 40 controls pacing therapy based on whether an electrical signal sensed on one of leads 24a,b coincides with an independently detected noise signal and occurred during a period of time in which an intrinsic cardiac signal is expected to occur. As will be described in further detail with respect to the flow diagram of FIGS. 4-6, control module 40 delivers a pacing pulse subsequent to sensing an electrical signal on the lead when the sensed electrical signal coincides with an independently detected noise signal and the sensed electrical signal occurs during a period of time of an expected intrinsic cardiac signal. Control module 40 may deliver the pacing pulse immediately after, e.g., within 100 milliseconds (ms), its determination that the sensed electrical signal coincides with an independently detected noise signal and occurs during a period of time of an expected intrinsic cardiac signal. In some instances, control module 40 may trigger delivery of the pacing pulse during the escape interval instead of waiting for the escape interval to expire.

When the sensed electrical signal on the lead does not coincide with a noise signal, control module 40 withholds (e.g., inhibits) delivery of a pacing pulse. When no signal is sensed during the escape interval, control module 40 delivers a pacing pulse at the expiration of the escape interval. When the sensed electrical signal on the lead does not occur during the period of time in which an intrinsic cardiac signal is expected to occur and coincides with a noise signal, control module 40 ignores sensing for the purposes of pacing therapy delivery. Pacing in accordance with the techniques of this disclosure may allow for improved therapy during an MRI procedure by decreasing the risk associated with inappropriate pacing inhibition as well as decreasing the risk associated with pacing during the vulnerable period of the cardiac cycle.

The techniques described in this disclosure provide several advantages over the techniques described in the '568 patent to Zeijlemaker and the '958 patent to Paul et al. As described above, the '568 patent describes processing sensed electrical events that coincide with both of the extrapolated cardiac events and the sensed gradient fields according to typical state of the art for control of therapy delivery to maintain physiological cardiac function until a consecutive count of noise events and "virtual" cardiac events exceeds a predetermined number. After the consecutive count of noise events and "virtual" cardiac events exceeds a predetermined number, electrical sensing is ignored and the device switches into pacing stimulation at a prescribed number of beats per minute. On the other hand, the pacing techniques of this disclosure do not process the sensed cardiac signals that occur during the intervals of time for expected intrinsic cardiac signals and coincide with the noise signals detected by noise detection module 46 according to typical state of the art limitations. Instead, control module 40 triggers pacing immediately after the sensed cardiac signal, which is opposite from the typical state of the art of inhibiting delivery of the pacing pulse and resetting the escape intervals in response to detecting a cardiac event. Providing this functionality will decrease the risk associated with inappropriate pacing inhibition The '958 patent to Paul et al. describes a demand pacemaker that responds to a message that electromagnetic interference (EMI) has been detected in the same manner that it would respond if it sensed that the heart of the patient has failed to perform an expected event, that is, by producing a pacing signal to pump the chamber in which heart signals are being sensed. When a heart event is sensed and it coincides with the EMI present flag, the pacemaker proceeds as if the patient needed assistance. In particular, the pacemaker of the '958 patent waits for the current escape time interval to be completed and generates a stimulus pulse after expiration of the escape time interval. To the contrary, control module 40 triggers pacing immediately after the sensed cardiac signal in accordance with the techniques of this disclosure. As such, control module 40 may trigger pacing during the escape time interval instead of waiting for the escape time interval to expire. Providing this functionality will decrease the risk associated pacing during the vulnerable period of the cardiac cycle.

Therapy module 44 may, under the control of control module 40, also be configured to generate and deliver cardioversion and defibrillation therapy to the heart. For example, in the event that control module 40 detects an atrial or ventricular tachyarrhythmia, control module 40 may load an ATP regimen from memory 50, and control therapy module 44 to implement the ATP regimen. Therapy module 44 may also include a high voltage charge circuit and a high voltage output circuit that generate high voltage shocks to defibrillate the heart.

In some instances, control module 40 may operate IMD 22 in accordance with the described pacing mode as a normal mode of operation. In this case, pacing in accordance with the techniques of this disclosure could also eliminate the service burden associated with manually programming an MRI safe mode of operation before and after a patient undergoes a MRI procedure. In other instances, control module 40 may operate IMD 22 to pace in accordance with the techniques of this disclosure when operating in an MRI mode. Control module 40 may also suspend temporary operation of other functionality of IMD 22 while operating in the MRI mode, including tachycardia detection and therapy, fibrillation detection and therapy, impedance measurements, battery measurements, or the like.

Control module 40 may transition operation of IMD 22 into the MRI mode upon detecting the presence of MRI device 16. IMD 22 may include one or more sensors, such as a magnetic field sensor 52, which detect presence of MRI device 16. Magnetic field sensor 52 may include a magnetic field detector, such as a Hall sensor or a reed switch. The signal produced by magnetic field sensor 52 may, for example, identify patient 12 has entered an MRI environment when the magnetic field is greater than or equal to a threshold level indicative of MRI device 16. Alternatively, control module 40 may transition operation of IMD 22 into the MRI mode manually before undergoing the MRI procedure. For example, a user, such as a physician, clinician or technician, may manually cause external device 34 to transmit a command that causes control module 40 to transition operation of IMD 22 into the MRI mode.

Figure 4:
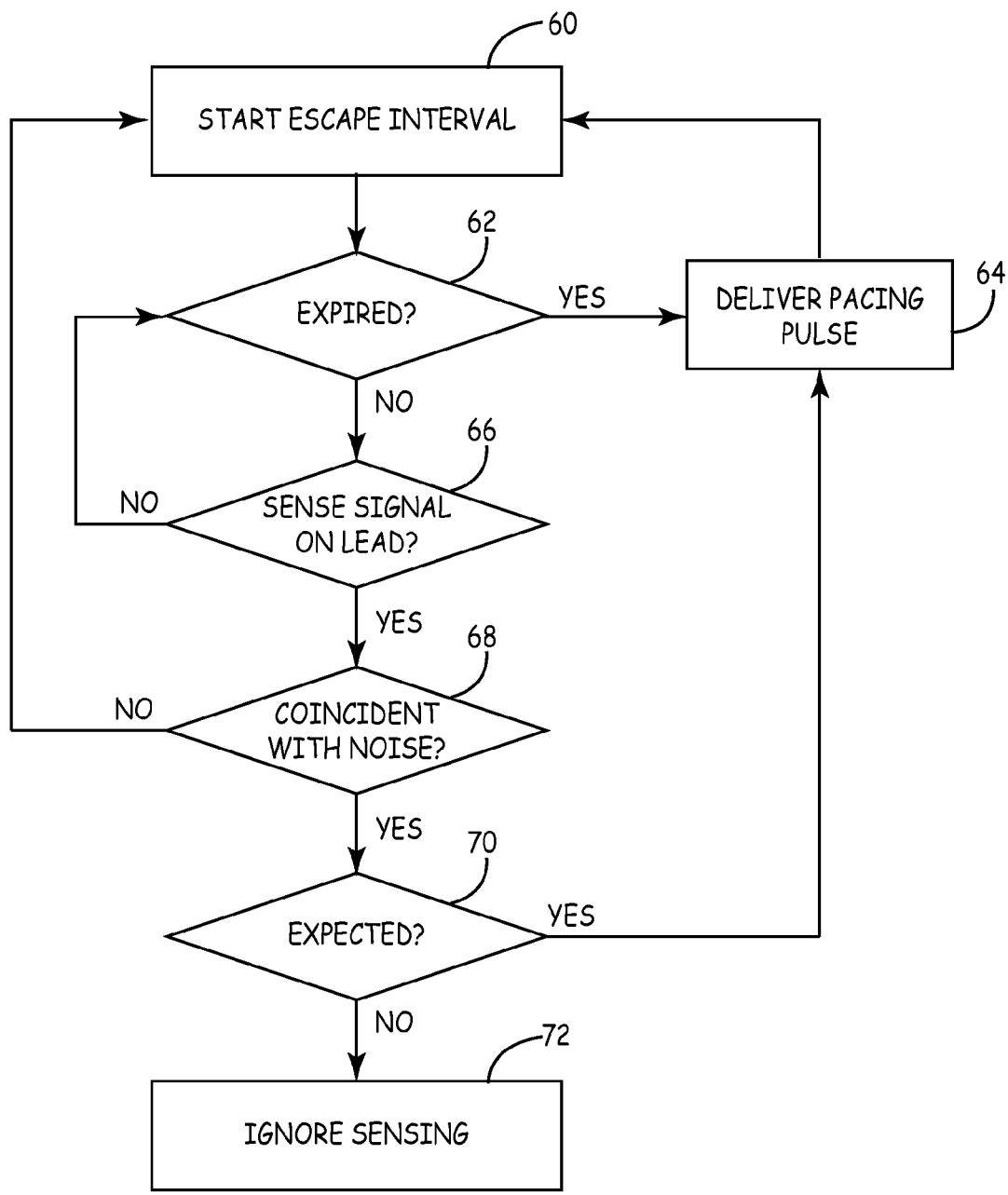
FIG. 4 is a flow diagram illustrating example operation of an implantable medical device triggering pacing based on determining whether the sensed electrical signal coincides with a sensed noise signal and determining whether the sensed electrical signal occurs during a period of time of an expected intrinsic cardiac signal.

FIG. 4 is a flow diagram illustrating example operation of an implantable medical device triggering pacing based on determining whether the sensed electrical signal coincides with a sensed noise signal and determining whether the sensed electrical signal occurs during a period of time of an expected intrinsic cardiac signal. FIG. 4 will be described with respect to implantable medical system 20 for purposes of discussion. However, the techniques may be implemented in any implantable medical device.

Initially, control module 40 of IMD 22 starts a pacing escape interval (60). As described above, the pacing escape interval defines a period of time during which IMD 22 waits to sense a cardiac event, such as an intrinsic cardiac depolarization of a respective chamber of the heart, before delivering a pacing pulse to the heart. Control module 40 determines whether the pacing escape interval has expired (62). Control module 40 determines that the pacing escape interval has expired when no electrical signal is sensed on the implantable medical lead for the period of time associated with the escape interval. When the pacing escape interval expires ("YES" branch of block 62), control module 40 controls therapy module 44 to deliver a pacing pulse (64).

When the pacing escape interval does not expire ("NO" branch of block 62), control module 40 determines whether an electrical signal is sensed on the implantable medical lead (66). When no electrical signal is sensed on the implantable medical lead ("NO" branch of block 66), control module 40 determines whether the pacing escape interval has expired (62). When an electrical signal is sensed on the implantable medical lead ("YES" branch of block 66), control module 40 determines whether the sensed electrical signal coincides with a noise signal (68). As described above, noise detection module 46 of IMD 22 detects noise signals independently of any signals sensed on leads 24a,b and provides the noise signals or indicates that noise signals are detected to control module 40. Control module 40 may compare the time at which the noise signals are sensed with the time at which the electrical signals are detected to determine whether the electrical signal and noise signal are coincident. The two signals may be coincident as long as they occur within a threshold period of time of one another. For example, control module 40 may determine the electrical signal sensed on the lead 24 and noise signal sensed via the noise detection module 46 are coincident when they both occur within 10 ms. However, values larger or smaller than 10 ms may be used.

When control module 40 determines that the sensed electrical signal does not coincide with the noise signal ("NO" branch of block 68), control module 40 restarts the escape interval (60). In some instances, the escape interval includes the refractory period. In other instances, control module 40 may initiate the refractory period timer in response to when control module 40 determines that the sensed electrical signal does not coincide with the noise signal and restart the escape interval after expiration of the refractory period timer.

When control module 40 determines that the sensed electrical signal coincides with the noise signal ("YES" branch of block 68), control module 40 determines whether the electrical signal occurs during a period of time in which an intrinsic cardiac signal is expected to occur (70). Control module 40 may analyze a recent history of cardiac electrophysiological data (including heart rate, heart rate variability, pacing percentage, and the like) to determine periods of time at which intrinsic cardiac signals are expected to occur.

When control module 40 determines that the electrical signal does not occur during a period of time in which an intrinsic cardiac signal is expected ("NO" branch of block 70), control module 40 ignores sensing for purposes of pacing therapy delivery (72). When control module 40 determines that the electrical signal does occur during a period of time in which an intrinsic cardiac signal is expected ("YES" branch of block 70), control module 40 controls therapy module 44 to deliver a pacing pulse (64). In this case, control module 40 does not wait for the escape interval to timeout. Instead, control module 40 causes the pacing pulse to be delivered substantially immediately after the determination, e.g., within 100 ms of sensing the electrical signal. Providing this functionality will decrease the risk associated with inappropriate pacing inhibition, as well as decrease the risk associated with pacing during the vulnerable period of the cardiac cycle.

Figure 5:
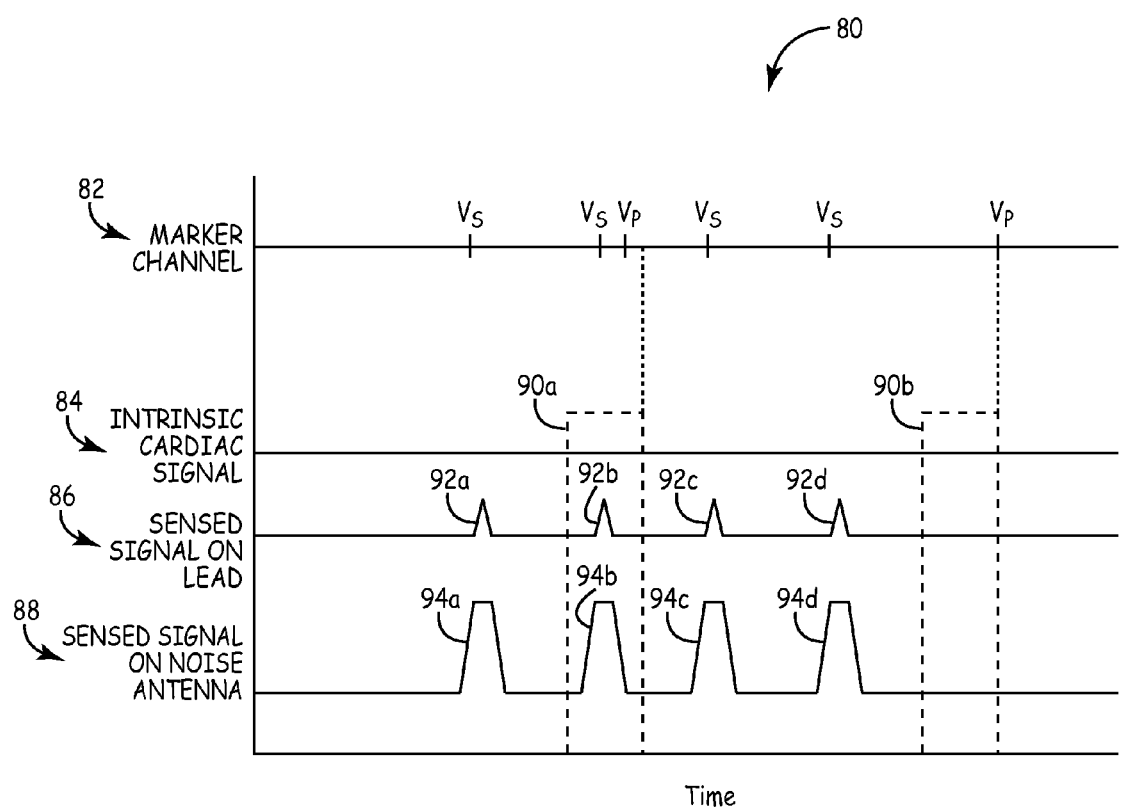
FIGS. 5 and 6 illustrate timing diagrams of the pacing techniques described herein.

FIG. 5 illustrates a timing diagram 80. Timing diagram 80 shows marker channel information (labeled 82), an intrinsic cardiac signal of the heart of a patient (labeled 84), an electrical signal sensed on a lead (labeled 86), and a noise signal sensed on antenna (labeled 88). Dashed boxes 90*a,b* represent the period of time in which an intrinsic cardiac signal is expected to occur. Timing diagram 80 is described with respect to a lead implanted within the ventricle of the patient for exemplary purposes.

In the example illustrated in FIG. 5, the patient has a slow or no underlying intrinsic rhythm, as evidenced by the intrinsic cardiac signal having no intrinsic cardiac electrical signals. Although there is no underlying intrinsic cardiac signal, sensing module 42 senses electrical signals 92*a-d* ("electrical signals 92") on the lead. As described above, sensing module 42 may detect electrical signals induced on the lead by external signals in addition to detecting intrinsic cardiac signals. In the example illustrated in FIG. 5, electrical signals 92 correspond with energy induced on the lead by noise, such as RF fields and/or gradient magnetic fields generated by MRI device 16 during an MRI procedure.

The sensed electrical signals 92 on the lead correspond with the sensed ventricular events (labeled $V_S$ in the marker channel information of FIG. 5). In other words, when the electrical signal sensed on the lead exceeds a threshold magnitude a sensed ventricular event is added to the marker channel information. Without more information, however, it is not possible to distinguish whether the electrical signals 92 and/or the sensed ventricular events ($V_S$) on the marker channel information correspond with intrinsic cardiac signals or noise signals.

To aid in differentiating intrinsic cardiac signals from noise signals, noise detection module 46 monitors signals sensed on antenna 58. As described above, noise detection module 46 monitors the noise signals independently of any of the electrical signals sensed on the lead. The signal sensed on antenna 58 includes noise signals 94*a-d* ("noise signals 94") sensed by noise detection module 46. In the example illustrated in FIG. 5, all of electrical signals 92 and sensed ventricular events ($V_s$) are caused by MRI-induced noise.

Control module 40 processes the signals received on the lead and the signals received on the antenna 58 in accordance with the techniques described above to control pacing therapy. For example, control module determines electrical signal 92*a* coincides with noise signal 94*a*. However, because electrical signal 92*a* does not occur during a period of time of an expected intrinsic cardiac signal (e.g., within one of boxes 90*a,b*), control module 40 characterizes electrical signal 92*a* as MRI-induced noise and not intrinsic cardiac activity. Control module 40 ignores sensed electrical signal 92*a* for purposes of therapy delivery because it does not occur during the period of time of the expected intrinsic cardiac signal. Control module 40 treats electrical signals 92*c* and 92*d* in the same manner as 92*a*.

Control module determines electrical signal 92*b* also coincides with noise (i.e., noise signal 94*b*). However, control module 40 also determines that electrical signal 92*b* occurs during a period of time of an expected intrinsic cardiac signal (e.g., within the period of time represented by box 90*a*). Control module 40 characterizes electrical signal 92*b* as indeterminate because control module 40 cannot be sure electrical signal 92*b* is caused by MRI-induced noise as an intrinsic cardiac signal may have also occurred at or near this time. Control module 40 therefore triggers delivery of a pacing pulse a short period of time after detecting electrical signal 92*b*. The delivered pacing pulse is represented as $V_P$ in the marker channel information of FIG. 5. Control module 40 may trigger delivery of the pacing pulse within 100 ms of electrical signal 92*b* to ensure pacing therapy is administered at a physiologically appropriate time. In the example illustrated in FIG. 5, control module 40 triggers delivery of the pacing pulse $V_P$ prior to expiration of the ventricular escape interval, which occurs at the end of the period of time represented by box 90*a*. Providing this functionality will decrease the risk associated with pacing during the vulnerable period of the cardiac cycle, e.g., pacing on the T-wave.

When control module 40 does not detect any electrical signals 92 on the lead, control module 40 triggers delivery of a pacing pulse at the expiration of the ventricular escape interval. Such a scenario is illustrated with reference to the period of time represented by box 90*b*. As such, pacing therapy is provided at the lower rate limit when no electrical signals 92 are detected on the lead.

Figure 6:
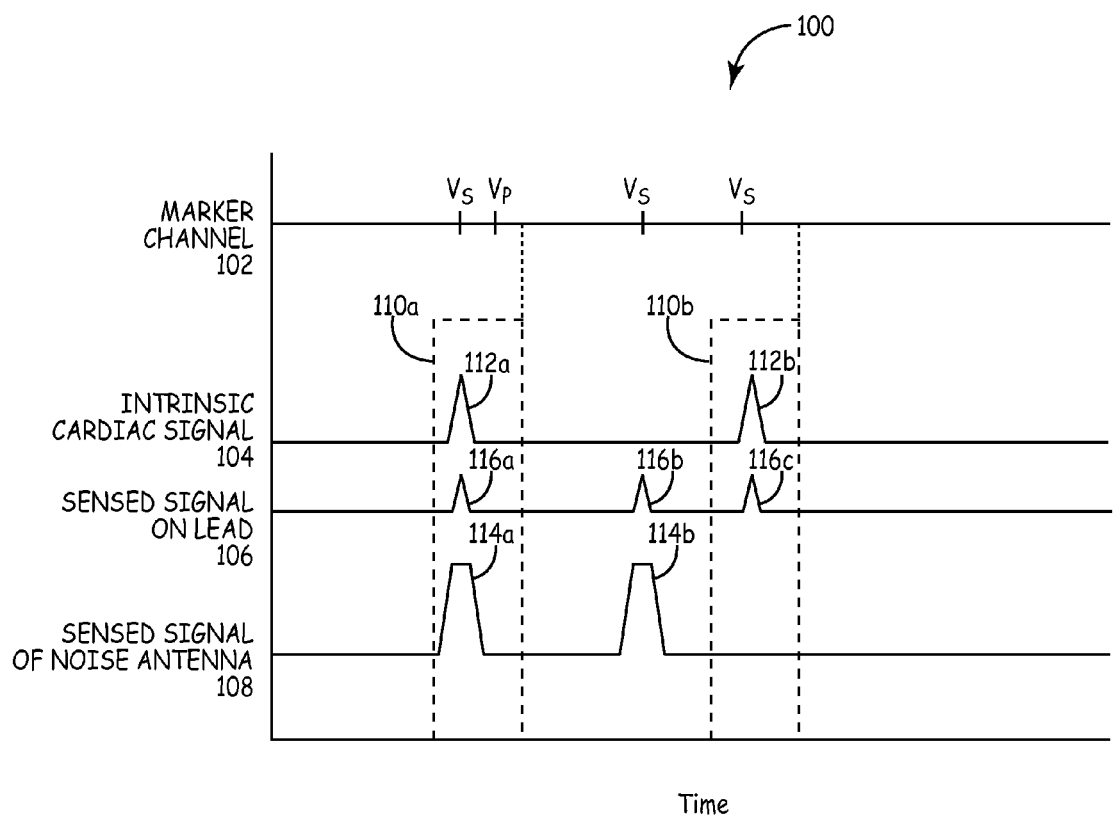

FIG. 6 illustrates a timing diagram 100. Timing diagram 100 shows marker channel information (labeled 102), an intrinsic cardiac signal of the heart of a patient (labeled 104), an electrical signal sensed on a lead (labeled 106), and a noise signal sensed on antenna (labeled 108). Dashed boxes 110*a,b* represent the period of time in which an intrinsic cardiac signal is expected to occur. Timing diagram 100 is described with respect to a lead implanted within the ventricle of the patient for exemplary purposes.

Unlike the example illustrated in FIG. 5, the patient has an underlying intrinsic heart rhythm in the example illustrated in FIG. 6. The intrinsic cardiac signal includes a number of intrinsic cardiac signals 112*a-b* ("intrinsic cardiac signals 112"). Noise detection module 46 also detects a number of noise signals 114*a-b* ("noise signals 114") on antenna 58. Sensing module 42 senses electrical signals 116*a-c* ("electrical signals 116") on the lead that correspond with either intrinsic cardiac signals 112, noise signals 114, or both. When sensing module 42 senses an electrical on the lead exceeds a threshold magnitude a sensed ventricular event (labeled $V_S$) is added to the marker channel information.

Without more information, however, control module 40 cannot distinguish whether electrical signals 116 and/or the corresponding sensed ventricular events ($V_S$) on the marker channel information correspond with intrinsic cardiac signals or noise signals. Control module 40 processes electrical signals 116 received on the lead and noise signals 114 received on antenna 58 in accordance with the techniques described above to better distinguish noise from intrinsic cardiac signals. In turn, control module 40 provides more accurate pacing therapy.

Control module 40 detects electrical signal 116*a* and determines that electrical signal 116*a* coincides with noise signal 114*a*. Additionally, control module 40 determines that electrical signal 116a occurs during a period of time of an expected intrinsic cardiac signal (e.g., within the period of time represented by box 110a). Control module 40 characterizes electrical signal 116a as indeterminate because control module 40 cannot be sure whether electrical signal 116a is caused by MRI-induced noise or is associated with an intrinsic cardiac signal that also occurred at or near this time. Control module 40 therefore triggers delivery of a pacing pulse a short period of time after detection of electrical signal 116a. The delivered pacing pulse is represented as $V_P$ in the marker channel information of FIG. 6. Control module 40 may trigger delivery the pacing pulse within 100 ms of electrical signal 116b to ensure pacing therapy is administered at a physiologically appropriate time. In the example illustrated in FIG. 6, control module 40 triggers delivery of the pacing pulse $V_P$ prior to expiration of the ventricular escape interval, which occurs at the end of the period of time represented by box 110a. Providing this functionality will decrease the risk associated pacing during the vulnerable period of the cardiac cycle, e.g., pacing on the T-wave.

Control module 40 detects electrical event 116b and determines that electrical event 116b coincides with noise signal 114b. However, because electrical signal 116b does not occur during a period of time of an expected intrinsic cardiac signal (e.g., within one of boxes 110a,b), control module 40 characterizes electrical signal 116b as MRI-induced noise and not intrinsic cardiac activity and ignores sensed electrical signal 116b for purposes of therapy delivery.

Control module 40 detects electrical event 116c and determines that electrical event 116c does not coincide with any noise signal detected on antenna 58. Because electrical signal 116c does not coincide with any noise signal detected on antenna 58, control module 40 may reliably determine that electrical signal 116c is associated with intrinsic cardiac activity. Control module 40 withholds delivery of a pacing pulse since electrical signal is associated with intrinsic cardiac activity.

The techniques described herein may be applicable to other therapy systems. For example, the techniques described herein may be applicable to systems including an IMD that delivers electrical stimulation therapy to other muscles, nerves or organs of patient 12. As another example, the techniques described herein may be applicable to systems including an implantable drug delivery or infusion device or an IMD including a drug delivery or infusion module. Other combinations of implantable devices will be obvious to one of skill in the art, and fall within the scope of this disclosure.

The techniques described in this disclosure, including those attributed to IMD 22, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, or flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   sensing an electrical signal on an implantable medical lead implanted within a chamber of a heart;
   determining whether the sensed electrical signal coincides with a sensed noise signal;
   determining whether the sensed electrical signal occurs during a period of time of an expected intrinsic cardiac signal; and
   triggering delivery of a pacing pulse on the implantable medical lead implanted within the chamber of the heart in which the electrical signal is sensed before expiration of an escape interval associated with the chamber of the heart in which the electrical signal is sensed when the sensed electrical signal coincides with a sensed noise signal and the sensed electrical signal occurs during the period of time of the expected intrinsic cardiac signal.

2. The method of claim 1, further comprising withholding delivery of a pacing pulse when the sensed electrical signal does not coincide with a sensed noise signal.

3. The method of claim 1, further comprising ignoring the sensed electrical signal for purposes of therapy delivery when the sensed electrical signal coincides with a sensed noise signal and does not occur during the period of time of the expected intrinsic cardiac signal.

4. The method of claim 1, further comprising triggering delivery of a pacing pulse on the implantable medical lead implanted within the chamber of the heart in which the electrical signal is sensed upon expiration of the escape interval associated with the chamber of the heart in which the electrical signal is sensed when no electrical signal is sensed on the implantable medical lead.

5. The method of claim 1, wherein triggering delivery of the pacing pulse before expiration of the escape interval associated with the chamber of the heart in which the electrical signal is sensed comprises triggering delivery of the pacing pulse within approximately one hundred (100) milliseconds after sensing the electrical event and prior to the expiration of the escape interval.

6. The method of claim 1, further comprising determining the period of time of the expected intrinsic cardiac signal based on stored data regarding recent cardiac electrophysiological activity.

7. The method of claim 6, wherein determining the period of time of the expected intrinsic cardiac signal based on stored data regarding recent cardiac electrophysiological activity comprises determining the period of time of the expected intrinsic cardiac signal based on stored data regarding at least one of recent heart rate, recent heart rate variability, and recent pacing percentage.

8. The method of claim 1, further comprising monitoring for the noise signal using a noise detection module that is separate from the sensing module used to sense the electrical signal of the implantable medical lead.

9. The method of claim 1, further comprising detecting a condition indicative of the presence of an MRI device and transitioning, in response to detecting the condition, to a pacing mode in which delivery of the pacing pulse is triggered before expiration of the escape interval when the sensed electrical signal coincides with a sensed noise signal and the sensed electrical signal occurs during the period of time of the expected intrinsic cardiac signal.

10. An implantable medical system comprising:
an implantable medical lead implanted within a chamber of a heart and including at least one electrode;
an implantable medical device comprising:
a noise detection module that detects noise signals;
a sensing module that detects an electrical signal of the chamber of the heart on the implantable medical lead;
a therapy module that delivers pacing therapy to the chamber of the heart via the implantable medical lead; and
a control module that determines whether the sensed electrical signal on the implantable medical lead implanted within the chamber of the heart coincides with a sensed noise signal, determines whether the sensed electrical signal occurs during a period of time of an expected intrinsic cardiac signal, and controls the therapy module to deliver a pacing pulse on the implantable medical lead implanted within the chamber of the heart before expiration of an escape interval associated with the chamber of the heart in which the electrical signal is sensed when the sensed electrical signal coincides with a sensed noise signal and the sensed electrical signal occurs during the period of time of the expected intrinsic cardiac signal.

11. The system of claim 10, wherein the control module withholds delivery of a pacing pulse when the sensed electrical signal does not coincide with a sensed noise signal.

12. The system of claim 10, wherein the control module ignores the sensed electrical signal for purposes of therapy delivery when the sensed electrical signal coincides with a sensed noise signal and does not occur during the period of time of the expected intrinsic cardiac signal.

13. The system of claim 10, wherein the control module triggers delivery of a pacing pulse upon expiration of the escape interval associated with the chamber of the heart in which the electrical signal is sensed when no electrical signal is sensed on the implantable medical lead.

14. The system of claim 10, wherein the control module triggers delivery of the pacing pulse within approximately one hundred (100) milliseconds after sensing the electrical event and prior to the expiration of the escape interval.

15. The system of claim 10, wherein the control module determines the period of time of the expected intrinsic cardiac signal based on stored data regarding recent cardiac electrophysiological activity.

16. The system of claim 15, wherein the control module determines the period of time of the expected intrinsic cardiac signal based on stored data regarding at least one of recent heart rate, recent heart rate variability, and recent pacing percentage.

17. The system of claim 10, further comprising a magnetic field sensor, wherein the control module detects a condition indicative of the presence of an MRI device based on the output of the magnetic field sensor and transitions, in response to detecting the condition, to a pacing mode in which delivery of the pacing pulse is triggered before expiration of the escape interval when the sensed electrical signal coincides with a sensed noise signal and the sensed electrical signal occurs during the period of time of the expected intrinsic cardiac signal.

18. The system of claim 10, wherein the chamber of the heart comprises a ventricle of the heart.

19. A computer-readable storage medium comprising instructions that, when executed, cause an implantable medical device to:
sense an electrical signal on an implantable medical lead implanted within a chamber of a heart;
determine whether the sensed electrical signal coincides with a sensed noise signal;
determine whether the sensed electrical signal occurs during a period of time of an expected intrinsic cardiac signal; and
trigger delivery of a pacing pulse on the implantable medical lead implanted within the chamber of the heart in which the electrical signal is sensed before expiration of an escape interval associated with the chamber of the heart in which the electrical signal is sensed when the sensed electrical signal coincides with a sensed noise signal and the sensed electrical signal occurs during the period of time of the expected intrinsic cardiac signal.

* * * * *